(12) United States Patent
Kida et al.

(10) Patent No.: US 12,047,677 B2
(45) Date of Patent: Jul. 23, 2024

(54) RADIATION IMAGING APPARATUS, RADIATION IMAGING SYSTEM, AND CONTROL METHOD OF RADIATION IMAGING APPARATUS

(71) Applicant: CANON KABUSHIKI KAISHA, Tokyo (JP)

(72) Inventors: Akira Kida, Kanagawa (JP); Motoki Tagawa, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 278 days.

(21) Appl. No.: 17/659,721

(22) Filed: Apr. 19, 2022

(65) Prior Publication Data

US 2022/0247927 A1 Aug. 4, 2022

Related U.S. Application Data

(63) Continuation of application No. PCT/JP2020/040835, filed on Oct. 30, 2020.

(30) Foreign Application Priority Data

Nov. 7, 2019 (JP) .................. 2019-202621

(51) Int. Cl.
*H04N 5/232* (2006.01)
*H04N 23/667* (2023.01)

(52) U.S. Cl.
CPC .................. *H04N 23/667* (2023.01)

(58) Field of Classification Search
CPC .................................................. H04N 23/667
See application file for complete search history.

(56) References Cited

U.S. PATENT DOCUMENTS 4,578,582 A * 3/1986 Takano .................. G01N 23/04
271/298
4,671,256 A * 6/1987 Lemelson .............. A61K 51/04
424/1.49

(Continued)

FOREIGN PATENT DOCUMENTS

CN 102918417 A 2/2013
CN 107440731 A 12/2017

(Continued)

OTHER PUBLICATIONS

Nakatsugawa translation of JP 2011252730 May 31, 2010 (Year: 2010).*

(Continued)

*Primary Examiner* — Zaihan Jiang
(74) *Attorney, Agent, or Firm* — VENABLE LLP

(57) ABSTRACT

A radiation imaging apparatus includes a first module including a first detection unit configured to detect radiation that has passed through an object; a second module including a second detection unit configured to detect the radiation that has passed through the object and the first detection unit; and a control unit configured to control the first module and the second module in accordance with a mode selected from a plurality of modes including a first mode in which each of the first detection unit and the second detection unit captures a radiation image, and a second mode in which, of the first detection unit and the second detection unit, the first detection unit captures a radiation image.

18 Claims, 9 Drawing Sheets

(56) References Cited

U.S. PATENT DOCUMENTS

| | | | | |
|---|---|---|---|---|
| 5,125,739 | A | * | 6/1992 | Suarez-Gonzalez ...... G01J 5/60 356/407 |
| 5,456,663 | A | * | 10/1995 | Lemelson .......... A61K 49/0004 604/890.1 |
| 5,882,330 | A | * | 3/1999 | Lemelson ............. A61K 51/04 604/890.1 |
| 8,439,031 | B1 | * | 5/2013 | Rothermel ........ A61M 16/0051 128/205.25 |
| 10,061,042 | B2 | | 8/2018 | Suzuki |
| 10,721,839 | B2 | | 7/2020 | Tagawa |
| 11,224,390 | B2 | | 1/2022 | Tagawa |
| 2002/0171816 | A1 | * | 11/2002 | Markle ............... G03F 7/70291 710/33 |
| 2007/0291904 | A1 | * | 12/2007 | Takenaka ............... G01N 23/04 378/207 |
| 2013/0119260 | A1 | | 5/2013 | Nakatsugawa |
| 2014/0103220 | A1 | | 4/2014 | Ohta |
| 2014/0252243 | A1 | * | 9/2014 | Ohguri .................. H04N 25/63 250/394 |
| 2015/0310597 | A1 | * | 10/2015 | Ohguri .................... A61B 6/00 382/275 |
| 2016/0307339 | A1 | * | 10/2016 | Miura .................. G06T 11/005 |
| 2016/0363675 | A1 | * | 12/2016 | Ohguri ..................... H04N 5/32 |
| 2017/0322619 | A1 | | 11/2017 | Eismann |
| 2018/0028141 | A1 | | 2/2018 | Kuwabara |
| 2019/0011576 | A1 | | 1/2019 | Kuwabara |
| 2022/0196859 | A1 | | 6/2022 | Fujiyoshi |
| 2023/0206404 | A1 | * | 6/2023 | Kobayashi ................ G06T 5/70 382/100 |

FOREIGN PATENT DOCUMENTS

| | | | |
|---|---|---|---|
| CN | 107661110 A | | 2/2018 |
| EP | 3226549 | * | 3/2017 |
| JP | 2001-133554 A | | 5/2001 |
| JP | 2011252730 | * | 5/2010 |
| JP | 2011-252730 A | | 12/2011 |
| JP | 2012-45044 A | | 3/2012 |
| JP | 2018-61763 A | | 4/2018 |
| WO | WO 2013015016 | * | 5/2012 |
| WO | 2013/015016 A1 | | 1/2013 |
| WO | WO-2013015016 | * | 1/2013 |
| WO | 2017/168849 A1 | | 10/2017 |

OTHER PUBLICATIONS

Ohta translation of WO 2013015016 May 31, 2012 (Year: 2012).*
Ryu translation of EP 3226549 Mar. 6, 2017 (Year: 2017).*
U.S. Appl. No. 17/708,256, Akira Kida, filed Mar. 30, 2022.

* cited by examiner

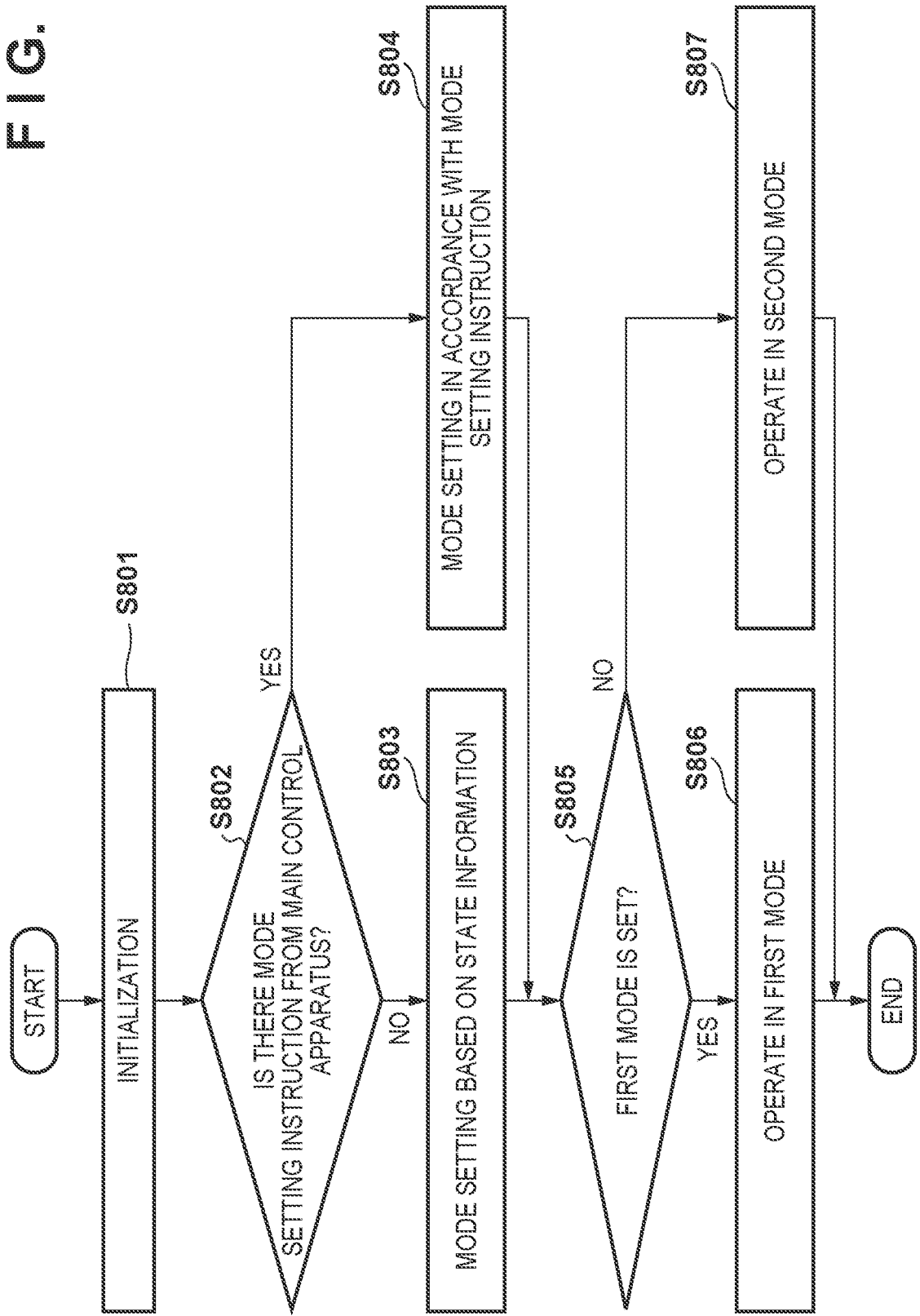

RADIATION IMAGING APPARATUS, RADIATION IMAGING SYSTEM, AND CONTROL METHOD OF RADIATION IMAGING APPARATUS

CROSS-REFERENCE TO RELATED APPLICATIONS

This application is a Continuation of International Patent Application No. PCT/JP2020/040835, filed Oct. 30, 2020, which claims the benefit of Japanese Patent Application No. 2019-202621, filed Nov. 7, 2019, both of which are hereby incorporated by reference herein in their entirety.

BACKGROUND OF THE INVENTION

Field of the Invention

The present invention relates to a radiation imaging apparatus, a radiation imaging system, and a control method of the radiation imaging apparatus.

Background Art

PTL 1 describes a radiation image capturing apparatus including a first radiation detector that detects radiation, and a second radiation detector that detects radiation that has passed through the first radiation detector. In the radiation image capturing apparatus, readout of charges accumulated in the second radiation detector is started before readout of charges accumulated in the first radiation detector. Also, in the radiation image capturing apparatus, when reading out charges accumulated in the second radiation detector, a control unit that controls readout of charges accumulated in the first radiation detector is set in a sleep state.

In PTL 1, only an operation of reading out both charges accumulated in the first radiation detector and charges accumulated in the second radiation detector is taken into consideration, and an operation of reading out only charges accumulated in one radiation detector is not taken into consideration. Hence, the application purpose of the radiation image capturing apparatus described in PTL 1 is limited, and versatility is low.

CITATION LIST

Patent Literature

PTL 1: WO 2017/168849.

SUMMARY OF THE INVENTION

The present invention provides a technique advantageous for improving the versatility of a radiation imaging apparatus.

One aspect of the present invention provides a radiation imaging apparatus comprising a first module including a first detection unit configured to detect radiation that has passed through an object, a second module including a second detection unit configured to detect the radiation that has passed through the object and the first detection unit, and a control unit configured to control the first module and the second module in accordance with a mode selected from a plurality of modes including a first mode in which each of the first detection unit and the second detection unit captures a radiation image, and a second mode in which, of the first detection unit and the second detection unit, the first detection unit captures a radiation image.

Further features of the present invention will become apparent from the following description of exemplary embodiments with reference to the attached drawings.

BRIEF DESCRIPTION OF THE DRAWINGS

FIG. 9 is a flowchart showing the operation of a radiation imaging apparatus 1 according to each of the first and second embodiments.

DESCRIPTION OF THE EMBODIMENTS

Figure 1:
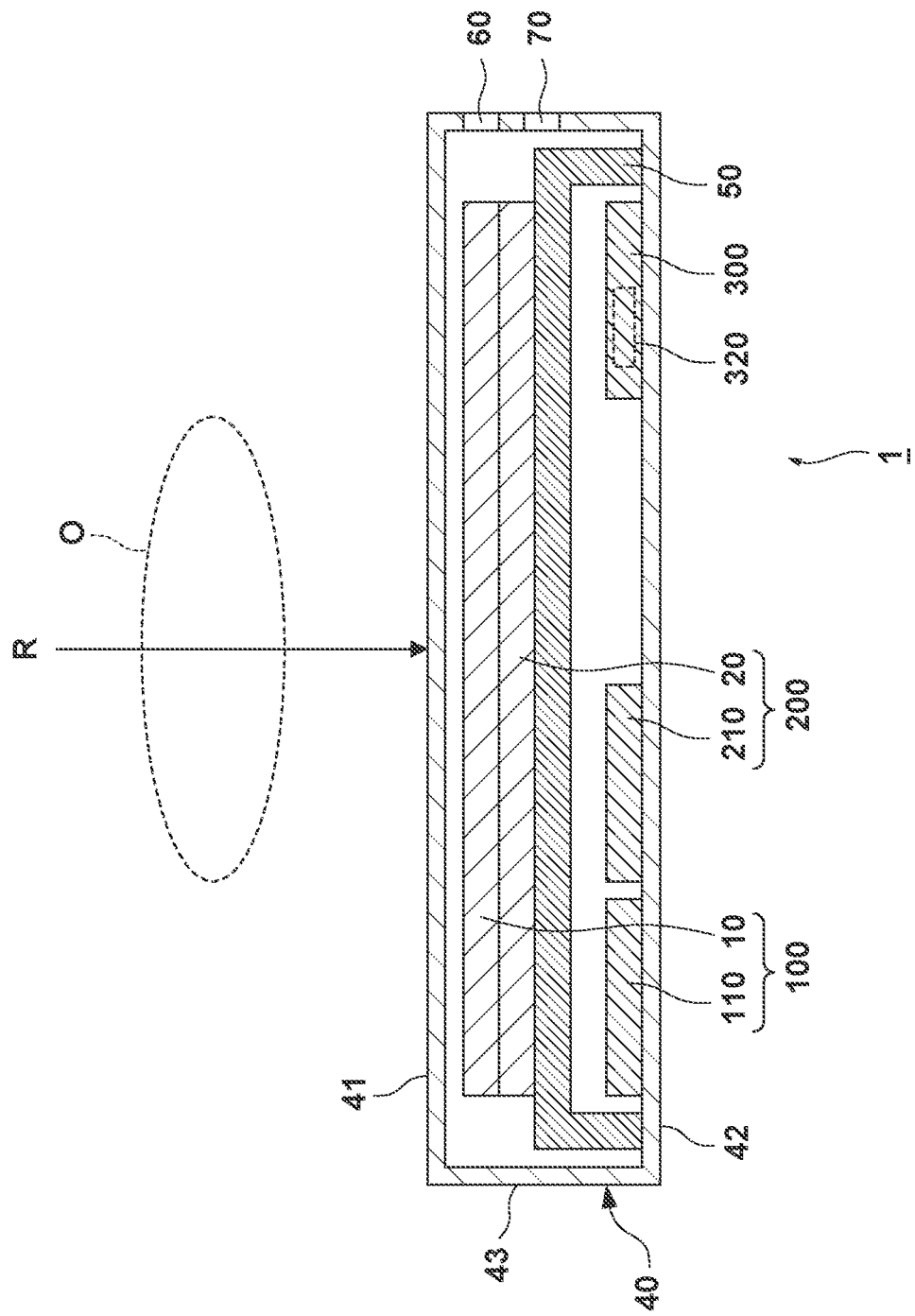
FIG. 1 is a sectional view showing the configuration of a radiation imaging apparatus according to an embodiment.

Hereinafter, embodiments will be described in detail with reference to the accompanying drawings. It should be noted that the following embodiments are not intended to limit the scope of the appended claims. A plurality of features are described in the embodiments, but not all of the plurality of features are necessarily essential to the present invention, and the plurality of features may arbitrarily be combined. The same reference numerals denote the same or similar parts in the accompanying drawings, and a repetitive description will be omitted.

FIG. 1 schematically shows the configuration of a radiation imaging apparatus 1 according to an embodiment. The radiation imaging apparatus 1 can include a first module 100 including a first detection unit 10 that detects radiation R that has passed through an object O, and a second module 200 including a second detection unit 20 that detects the radiation R that has passed through the object O and the first detection unit 10. The first detection unit 10 detects the radiation R entering the first detection unit 10 as a radiation image. The second detection unit 20 detects the radiation R entering the second detection unit 20 as a radiation image. The term "radiation" can include not only X-rays but also, for example, α-rays, β-rays, γ-rays, particle beams, and cosmic rays.

The radiation imaging apparatus 1 can include a main drive circuit 300 including a main control unit (control unit) 320 that controls the first module 100 and the second module 200. The main control unit 320 can control the first module 100 and the second module 200 in accordance with a mode selected from a plurality of modes including a first mode and a second mode. The plurality of modes may include one or a plurality of other modes (for example, a third mode).

The first mode can be a mode in which radiation images are captured by the first detection unit 10 and the second detection unit 20. In another viewpoint, the first mode can be a mode in which radiation is detected as radiation images by the first detection unit 10 and the second detection unit 20, and the signals (radiation images) detected by the first detection unit 10 and the second detection unit 20 are output. The second mode can be a mode in which, of the first detection unit 10 and the second detection unit 20, (only) the first detection unit 10 captures a radiation image. In another viewpoint, the second mode can be a mode in which, of the first detection unit 10 and the second detection unit 20, (only) the first detection unit 10 detects radiation as a radiation image and outputs the detected signal (radiation image).

The first mode can be a mode used to generate an image by, for example, an energy subtraction method. The energy subtraction method is a method for generating, based on a first image formed by radiation within a first energy range and a second image formed by radiation within a second energy range, a third image different from both the first image and the second image. Here, the first energy range and the second energy range are energy ranges different from each other. The first energy range and the second energy range may not have energy ranges overlapping each other, or a part of the first energy range and a part of the second energy range may overlap each other. In the second mode, of the first detection unit 10 and the second detection unit 20, (only) the first detection unit 10 can capture a still image or a moving image. A moving image can be formed by a plurality of images captured at a predetermined frame rate. In an example, the power consumption of the second module 200 in the second mode is smaller than the power consumption of the second module 200 in the first mode.

The first detection unit 10 can include a plurality of first pixels each configured to convert the radiation R within the first energy range into an electrical signal. In an example, the first detection unit 10 can include a first scintillator configured to convert the radiation R within the first energy range into light such as visible light, and a plurality of conversion elements each configured to convert the light converted by the first scintillator into an electrical signal. Each conversion element of the first detection unit 10 can form one first pixel. The first scintillator can be shared by the plurality of first pixels. The second detection unit 20 can include a plurality of second pixels each configured to convert the radiation R within the second energy range into an electrical signal. In an example, the second detection unit 20 can include a second scintillator configured to convert the radiation R within the second energy range into light such as visible light, and a plurality of conversion elements each configured to convert the light converted by the second scintillator into an electrical signal. Each conversion element of the second detection unit 20 can form one second pixel. The second scintillator can be shared by the plurality of second pixels.

The first module 100 can include not only the first detection unit 10 but also a drive circuit that drives the first detection unit 10. The second module 200 can include not only the second detection unit 20 but also a drive circuit that drives the second detection unit 20. The main drive circuit 300 can include not only the main control unit 320 but also a power supply circuit including a main power supply 310.

The radiation imaging apparatus 1 includes a housing 40, and the housing 40 can include a first plate portion 41, a second plate portion 42, and a side plate portion 43. The first plate portion 41 and the second plate portion 42 are arranged facing each other, and the side plate portion 43 connects the first plate portion 41 and the second plate portion 42. The first plate portion 41, the second plate portion 42, and the side plate portion 43 define an internal space separated from the external space, and the first module 100, the second module 200, and the main drive circuit 300 are arranged in the internal space. The first plate portion 41 includes an incident surface in which radiation enters via the object O. The first detection unit 10 is arranged between the first plate portion 41 and the second detection unit 20. The first detection unit 10 and the second detection unit 20 can be supported by a support body 50 connected to the housing 40.

The first detection unit 10 and a first drive circuit 110 can electrically be connected by a connecting portion such as a flexible cable. The second detection unit 20 and a second drive circuit 210 can electrically be connected by a connecting portion such as a flexible cable. The first drive circuit 110 can electrically be connected to the main drive circuit 300 by a connecting portion such as a flexible cable. The second drive circuit 210 can electrically be connected to the main drive circuit 300 by a connecting portion such as a flexible cable. The first drive circuit 110, the second drive circuit 210, and the main drive circuit 300 may be formed by one board, or may be formed by a plurality of boards.

The radiation imaging apparatus 1 may include a switch 60 configured to set the mode of the radiation imaging apparatus 1. Also, the radiation imaging apparatus 1 may include a display unit 70 configured to display the mode set in the radiation imaging apparatus 1. The switch 60 and the display unit 70 can be arranged on the housing 40, for example, the side plate portion 43.

Figure 2:
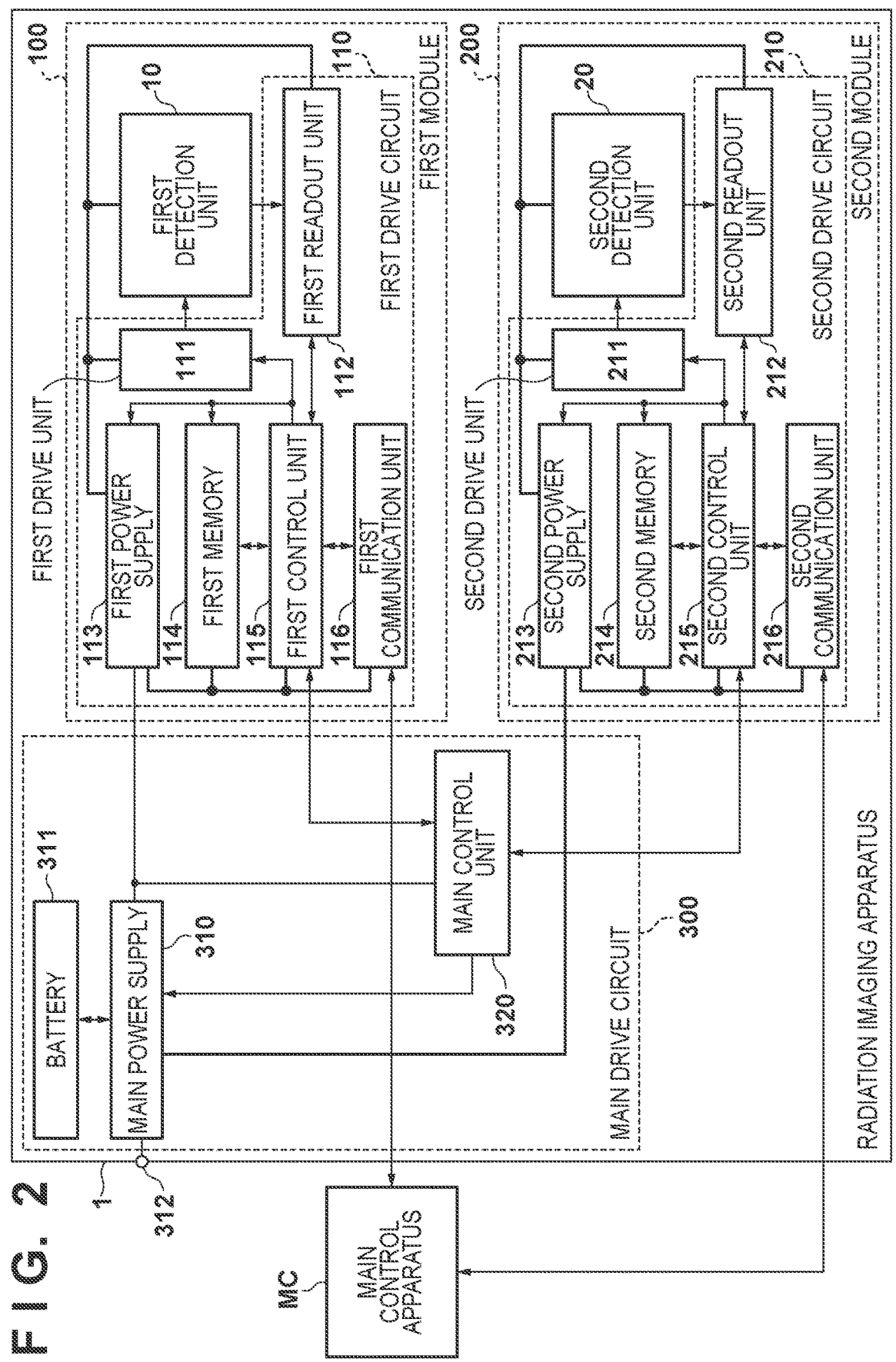
FIG. 2 is a view showing an example of the configuration of the radiation imaging apparatus according to the first embodiment.

FIG. 2 shows an example of the configuration of the radiation imaging apparatus 1 according to the first embodiment. The radiation imaging apparatus 1 can be configured to communicate with a main control apparatus (information processing apparatus) MC as an external apparatus wirelessly or by wire. The main control apparatus MC can function as a control apparatus that controls the radiation imaging apparatus 1, and as an information processing apparatus that processes a signal supplied from the radiation imaging apparatus 1. The main control apparatus MC can include, for example, an operation unit (console) to be operated by a user, a first interface configured to connect a radiation source (not shown) wirelessly or by wire, and a second interface configured to connect the radiation imaging apparatus 1 wirelessly or by wire. The main control apparatus MC can receive, via the second interface, the signal of an image captured by the radiation imaging apparatus 1 and process it. This processing can include, for example, processing of generating a new image by the above-described subtraction method. The main control apparatus MC can be formed by, for example, a general-purpose or dedicated computer with a program installed, or a combination of some or all of these.

In an example, a first signal (first image) detected by the first detection unit 10 and a second signal (second image) detected by the second detection unit 20 can be output (transferred) from the radiation imaging apparatus 1 to the main control apparatus MC. In this case, the main control apparatus MC can generate a third signal (third image) by energy subtraction based on the first signal and the second signal. In another example, the main control unit 320 can generate the third signal (third image) by energy subtraction based on the first signal (first image) detected by the first detection unit 10 and the second signal (second image) detected by the second detection unit 20.

The first drive circuit 110 of the first module 100 can include, for example, a first drive unit 111 that drives the first detection unit 10, and a first read unit 112 that reads out a signal from the first detection unit 10. The first detection unit 10 can include a plurality of first pixels arranged to form a plurality of rows and a plurality of columns. Each first pixel can include, for example, a conversion element, and a switch that controls electrical connection and disconnection between the conversion element and a column signal line. The first drive unit 111 can include, for example, a scanning circuit configured to scan the plurality of rows of the first detection unit 10, and a driver that drives the plurality of rows based on the output of the scanning circuit. The driver can generate a drive signal for driving the switches of the first pixels of a corresponding row. The first read unit 112 can include a plurality of column circuits that read out the signals of the first pixels in parallel from the plurality of columns of the first detection unit 10, and a multiplexer (column selection circuit) that sequentially selects and outputs the signals of the plurality of columns read out by the column circuits.

The first drive circuit 110 can further include at least one of a first power supply 113, a first memory 114, a first control unit 115, and a first communication unit 116. The first power supply 113 can supply power not only to the first detection unit 10 but also to constituent elements in the first drive circuit 110, for example, the first drive unit 111, the first read unit 112, the first memory 114, the first control unit 115, and the first communication unit 116.

The main drive circuit 300 can include the main power supply 310, and the first power supply 113 can supply power to the first detection unit 10 and the constituent elements in the first drive circuit 110 based on the power supplied from the main power supply 310. The first power supply 113 can include, for example, a DC/DC converter. The first memory 114 can store a signal read out from the first detection unit 10 by the first read unit 112. The main drive circuit 300 can include the main control unit 320, and the first control unit 115 can control the constituent element of the first module 110 in accordance with an instruction from the main control unit 320. The first control unit 115 can control the first drive unit 111 and the first read unit 112 in accordance with an instruction from the main control unit 320 such that the first detection unit 10 accumulates charges corresponding to incident radiation, and a signal corresponding to the charges is read out from the first detection unit 10 by the first read unit 112. The first communication unit 116 can communicate with the main control apparatus MC. More specifically, the first communication unit 116 can receive an instruction from the main control apparatus MC, or transmit, to the main control apparatus MC, a signal read out by the first read unit 112 and information representing the state of the first module 100.

The second module 200 can have the same configuration as the first module 100. More specifically, the second module 200 can include the second drive circuit 210. The second drive circuit 210 can include, for example, a second drive unit 211 that drives the second detection unit 20, and a second read unit 212 that reads out a signal from the second detection unit 20. The second detection unit 20 can include a plurality of second pixels arranged to form a plurality of rows and a plurality of columns. Each second pixel can include, for example, a conversion element, and a switch that controls electrical connection and disconnection between the conversion element and a column signal line. The second drive unit 211 can include, for example, a scanning circuit configured to scan the plurality of rows of the second detection unit 20, and a driver that drives the plurality of rows based on the output of the scanning circuit. The driver can generate a drive signal for driving the switches of the second pixels of a corresponding row. The second read unit 212 can include a plurality of column circuits that read out the signals of the second pixels in parallel from the plurality of columns of the second detection unit 20, and a multiplexer (column selection circuit) that sequentially selects and outputs the signals of the plurality of columns read out by the column circuits.

The second drive circuit 210 can further include at least one of a second power supply 213, a second memory 214, a second control unit 215, and a second communication unit 216. The second power supply 213 can supply power not only to the second detection unit 20 but also to constituent elements in the second drive circuit 210, for example, the second drive unit 211, the second read unit 212, the second memory 214, the second control unit 215, and the second communication unit 216.

The second power supply 213 can supply power to the second detection unit 20 and the constituent elements in the second module 200 based on the power supplied from the main power supply 310. The second power supply 213 can include, for example, a DC/DC converter. The second memory 214 can store a signal read out from the second detection unit 20 by the second read unit 212. The second control unit 215 can control the constituent element of the second drive circuit 210 in accordance with an instruction from the main control unit 320. The second control unit 215 can control the second drive unit 211 and the second read unit 212 in accordance with an instruction from the main control unit 320 such that the second detection unit 20 accumulates charges corresponding to incident radiation, and a signal corresponding to the charges is read out from the second detection unit 20 by the second read unit 212. The second communication unit 216 can communicate with the main control apparatus MC. More specifically, the second communication unit 216 can receive an instruction from the main control apparatus MC, or transmit, to the main control apparatus MC, a signal read out by the second read unit 212 and information representing the state of the second module 200.

The main drive circuit 300 can include the main power supply 310 in addition to the main control unit 320. The radiation imaging apparatus 1 or the main drive circuit 300 can include a connector 312 to which power is supplied via a power supply cable, and the main power supply 310 can supply power to the first power supply 113 and the second power supply 213 based on the power supplied to the connector 312. The power supplied to the connector 312 may be AC power or DC power. The connector 312 and the main power supply 310 may be stored in a housing different from that for the remaining portion of the radiation imaging apparatus 1. If the power supplied to the connector 312 is AC power, the main power supply 310 can include an AC/DC converter. If the power supplied to the connector 312 is DC power, the main power supply 310 can include a DC/DC converter. The first power supply 113 and the second power supply 213 may each be replaced with, for example, a switch such as a relay.

A battery 311 may be connected to the main power supply 310. If no power is supplied to the connector 312, the main power supply 310 can supply power to the first power supply 113 and the second power supply 213 based on power output from the battery 311. If power is supplied to the connector 312, and the remaining amount (accumulated power amount) of the battery 311 is less than a predetermined value, the main power supply 310 can charge the battery 311 using the power supplied to the connector 312. The remaining amount of the battery 311 can be detected based on the output voltage of the battery 311. Alternatively, the remaining amount of the battery 311 may be detected by detecting the power supply capability of the battery 311. The main power supply 310 can supply the power to the main control unit 320 as well. The function of the main control unit 320 may be replaced with the first control unit 115, and in this case, the main control unit 320 is unnecessary.

In the first mode, both the first detection unit 10 and the second detection unit 20 capture radiation images and output the captured radiation images. In the first mode, the first power supply 113 can supply power to the first detection unit 10 and the constituent element in the first drive circuit 110, and the second power supply 213 can supply power to the second detection unit 20 and the constituent element in the second drive circuit 210. In the second mode, of the first detection unit 10 and the second detection unit 20, the first detection unit 10 captures a radiation image and outputs the captured radiation image. Power supplied to at least one constituent element of the plurality of constituent elements of the second module 200 in the second mode can be made smaller than power supplied to the at least one constituent element in the first mode.

Figure 3:
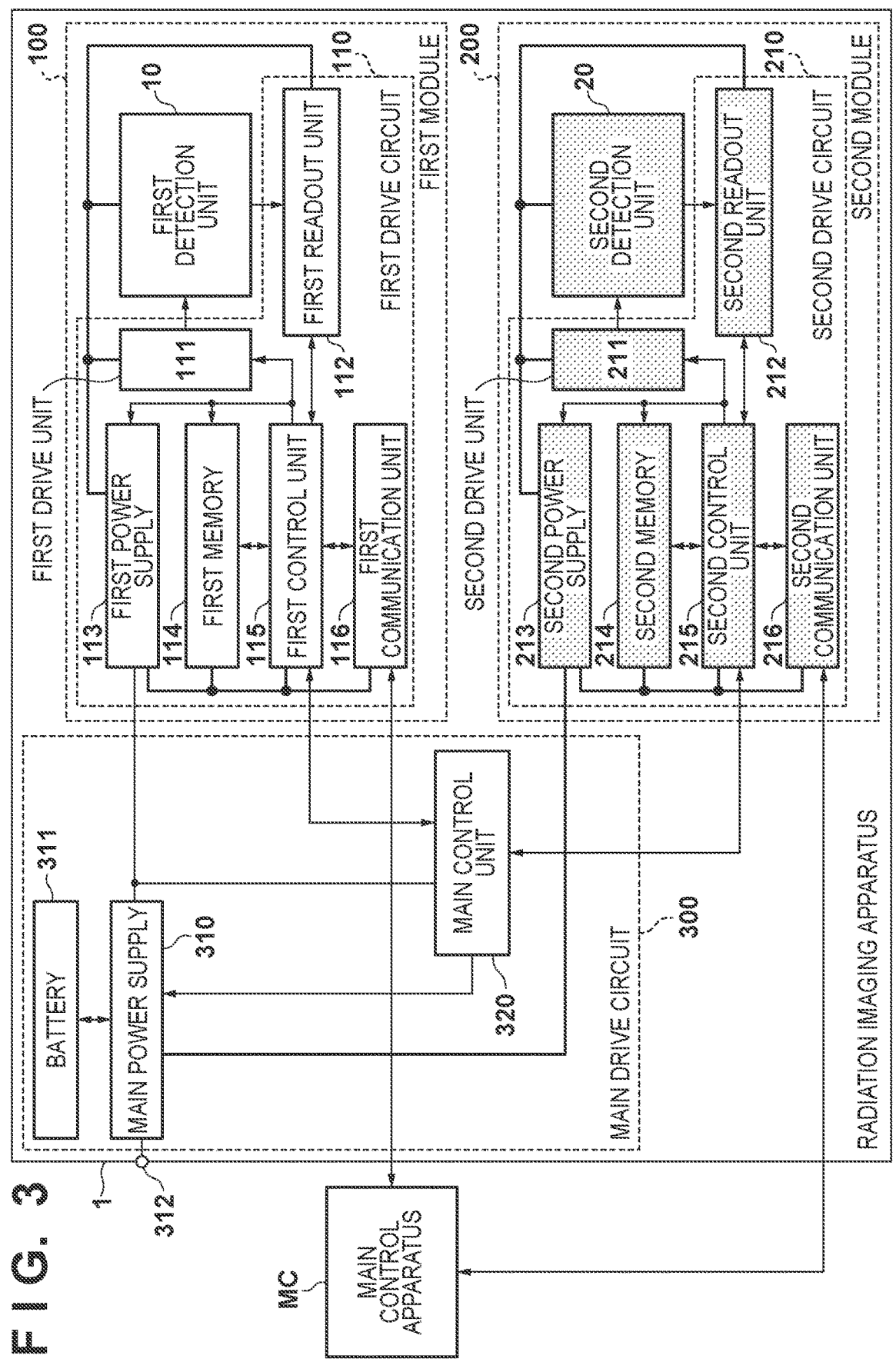
FIG. 3 is a view showing a first example of power supply in a second mode to a second module according to the first embodiment.

FIG. 3 shows a first example of power supply in the second mode to the second module 200 according to the first embodiment. Here, in FIG. 3, power supplied to the constituent elements shown in gray in the second mode is smaller than power supplied to the constituent elements in the first mode, and is, for example, zero. For example, the power consumption of the second detection unit 20, the second drive unit 211, and the second read unit 212 in the second mode is smaller than the power consumption of the second detection unit 20, the second drive unit 211, and the second read unit 212 in the first mode.

In the first example, the main control unit 320 can operate to operate the first power supply 113 and the second power supply 213 in the first mode, and to operate the first power supply 113 but not the second power supply 213 in the second mode. Focusing on the second power supply 213, the main control unit 320 can operate to operate the second power supply 213 in the first mode but not to operate the second power supply 213 in the second mode. This operation can be implemented by the main control unit 320 supplying a control signal to the second power supply 213 and the second power supply 213 operating in accordance with the control signal. Alternatively, this operation may be implemented by arranging a switch in the power supply path from the main power supply 310 to the second module 200 and the main control unit 320 controlling the switch.

Figure 4:
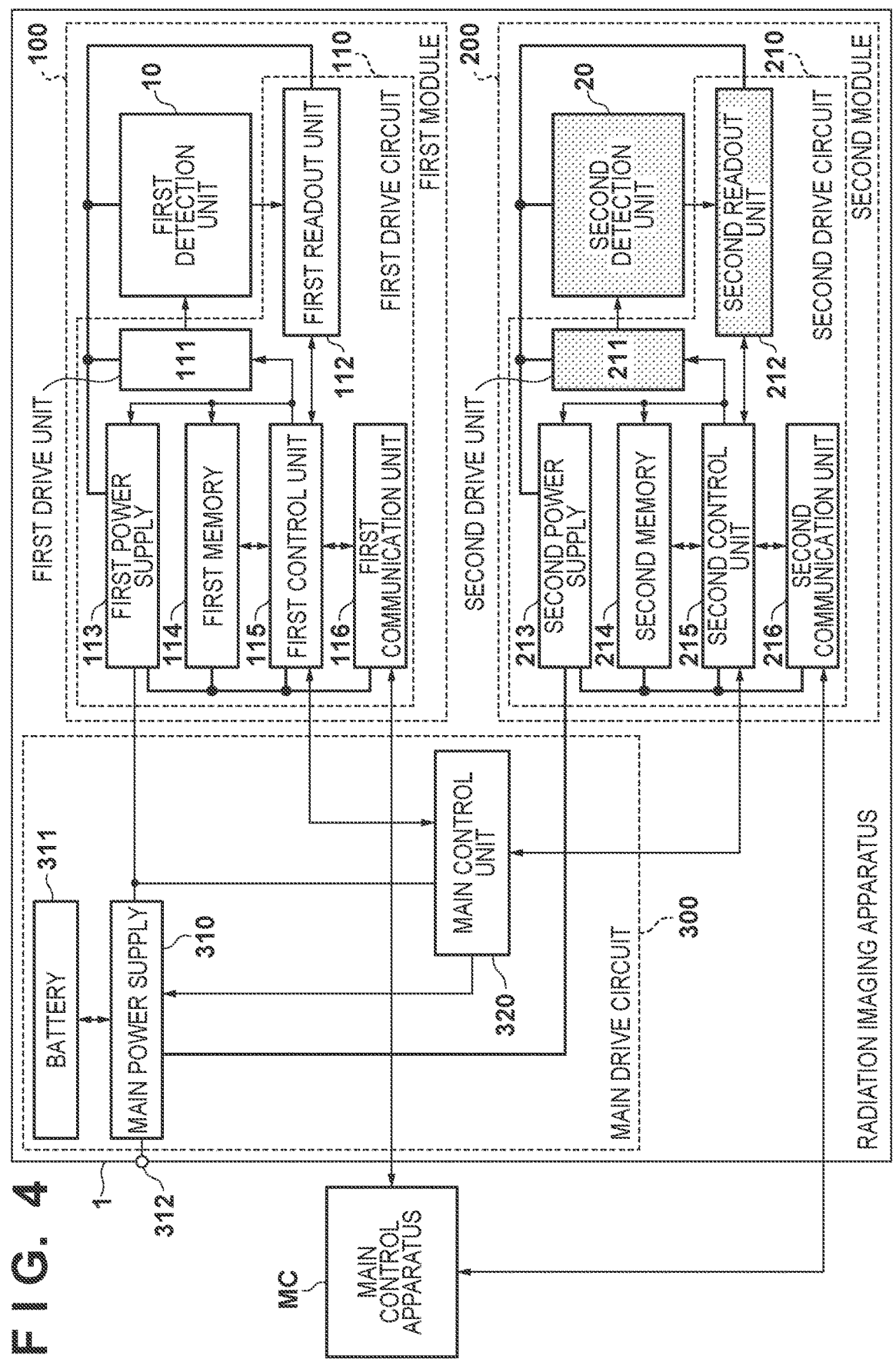
FIG. 4 is a view showing a second example of power supply in the second mode to the second module according to the first embodiment.

FIG. 4 shows a second example of power supply in the second mode to the second module 200 according to the first embodiment. Here, in FIG. 4, power supplied to the constituent elements shown in gray in the second mode is smaller than power supplied to the constituent elements in the first mode, and is, for example, zero. In the second example as well, the main control unit 320 controls the second module 200 such that the power consumption of the second detection unit 20, the second drive unit 211, and the second read unit 212 in the second mode is smaller than the power consumption of the second detection unit 20, the second drive unit 211, and the second read unit 212 in the first mode. In the second example, the second power supply 213 can supply power to the second memory 214, the second control unit 215, and the second communication unit 216 in the second mode, as in the first mode.

This operation can be implemented by the main control unit 320 supplying a control signal to the second power supply 213 and the second power supply 213 operating in accordance with the control signal. Alternatively, this operation can be implemented by the main control unit 320 supplying a control signal to the second control unit 215 and the second control unit 215 controlling the operations of the second detection unit 20, the second drive unit 211, and the second read unit 212 in accordance with the control signal.

In the first mode, the main control unit 320 can operate the first control unit 115 to temporarily store, in the first memory 114, the signal of the image read out from the first detection unit 10 by the first read unit 112. In addition, in the first mode, the main control unit 320 can control the second control unit 215 to temporarily store, in the second memory 214, the signal of the image read out from the second detection unit 20 by the second read unit 212. On the other hand, in the second mode, the main control unit 320 can operate the first control unit 115 to divided the signal of the image read out from the first detection unit 10 by the first read unit 112 and temporarily store the signals in the first memory 114 and the second memory 214. Here, a time needed to divide the signal of one image read out from the first detection unit 10 by the first read unit 112 and process the signals in parallel to store these in the first memory 114 and the second memory 214 in the second mode is defined as T2. In addition, a time needed to store, in the first memory 114, the signal of one image read out from the first detection unit 10 by the first read unit 112 in the first mode is defined as T1. In this case, the time T2 can be shorter than the time T1.

In the first mode, the main control unit 320 can operate the first control unit 115 to transfer, by the first communication unit 116, the signal of the image read out from the first detection unit 10 by the first read unit 112 to the main control apparatus MC. In addition, in the first mode, the main control unit 320 can operate the second control unit 215 to transfer, by the second communication unit 216, the signal of the image read out from the second detection unit 20 by the second read unit 212 to the main control apparatus MC. On the other hand, in the second mode, the main control unit 320 can operate the first control unit 115 and the second control unit 215 to divide the signal of the image read out from the first detection unit 10 by the first read unit 112 and transfer the signals to the main control apparatus MC by the first communication unit 116 and the second communication unit 216. Here, a time needed to divide the signal of one image read out from the first detection unit 10 by the first read unit 112 and transfer these to the main control apparatus MC by the first communication unit 116 and the second communication unit 216 in the second mode is defined as T3. In addition, a time needed to transfer the signal of one image read out from the first detection unit 10 by the first read unit 112 to the main control apparatus MC by the first communication unit 116 in the first mode is defined as T4. In this case, the time T3 can be shorter than the time T4.

If the second detection unit 20 is not driven in the second mode, a long time may be needed to stabilize the imaging operation by the second detection unit 20 immediately after transition for the second mode to the first mode. In the second mode, the main control unit 320 may reset the first detection unit 10 and the second detection unit 20 at a predetermined cycle during the period of waiting for radiation irradiation. Reset is an operation of turning on/off the switch of each pixel in the first detection unit 10 and the second detection unit 20 and resetting dark charges accumulated in the conversion elements. Here, in the first mode, the main control unit 320 can control the first control unit 115 and the second control unit 215 such that the first detection unit 10 and the second detection unit 20 are reset at a first cycle during the period of waiting for radiation irradiation. In the second mode, the main control unit 320 can control the second control unit 215 such that the second detection unit 20 is reset at a second cycle larger than the first cycle during the period of waiting for radiation irradiation. Also, in the second mode, the main control unit 320 can control the first control unit 115 such that the first detection unit 10 is reset at the first cycle during the period of waiting for radiation irradiation.

Reset of the first detection unit 10 can be performed by sequentially setting a plurality of drive signals corresponding to the plurality of rows of the first detection unit 10 to active level by the first drive unit 111 while maintaining the column signal line of the first detection unit 10 at a reset potential by the first read unit 112. A time needed to set all the plurality of rows to the active level is one cycle. The cycle corresponds to the period from ON input of the switch of each pixel to the next ON input. This also applies to reset of the second detection unit 20. Reset of the second detection unit 20 can be performed by sequentially setting a plurality of drive signals corresponding to the plurality of rows of the second detection unit 20 to active level by the second drive unit 211 while maintaining the column signal line of the second detection unit 20 at a reset potential by the second read unit 212.

As the driving method for reset of the second detection unit 20, not only a driving method of sequentially setting the plurality of rows to the active level but also a driving method of simultaneously setting all the plurality of rows to the active level can be used. When resetting the first detection unit 10 and the second detection unit 20 by the same driving method or different driving methods, in the second mode, the interval of ON of the switch of each pixel to the next ON is larger in the second cycle of the second detection unit than in the first cycle of the first detection unit 10. In addition, the OFF period between ON of the switch and next ON is preferably long. During reset of the first detection unit 10 and the second detection unit 20, a reset pulse of active level can be supplied to the reset switch of the integrating amplifier of each of the first read unit 112 and the second read unit 212 to reset-potential the column signal line to the reference potential of the integrating amplifier. Circuits (for example, the multiplexer and the A/D converter) after the integrating amplifier of the second read unit 212 need not be operated, and this can reduce power consumption.

Figure 5:
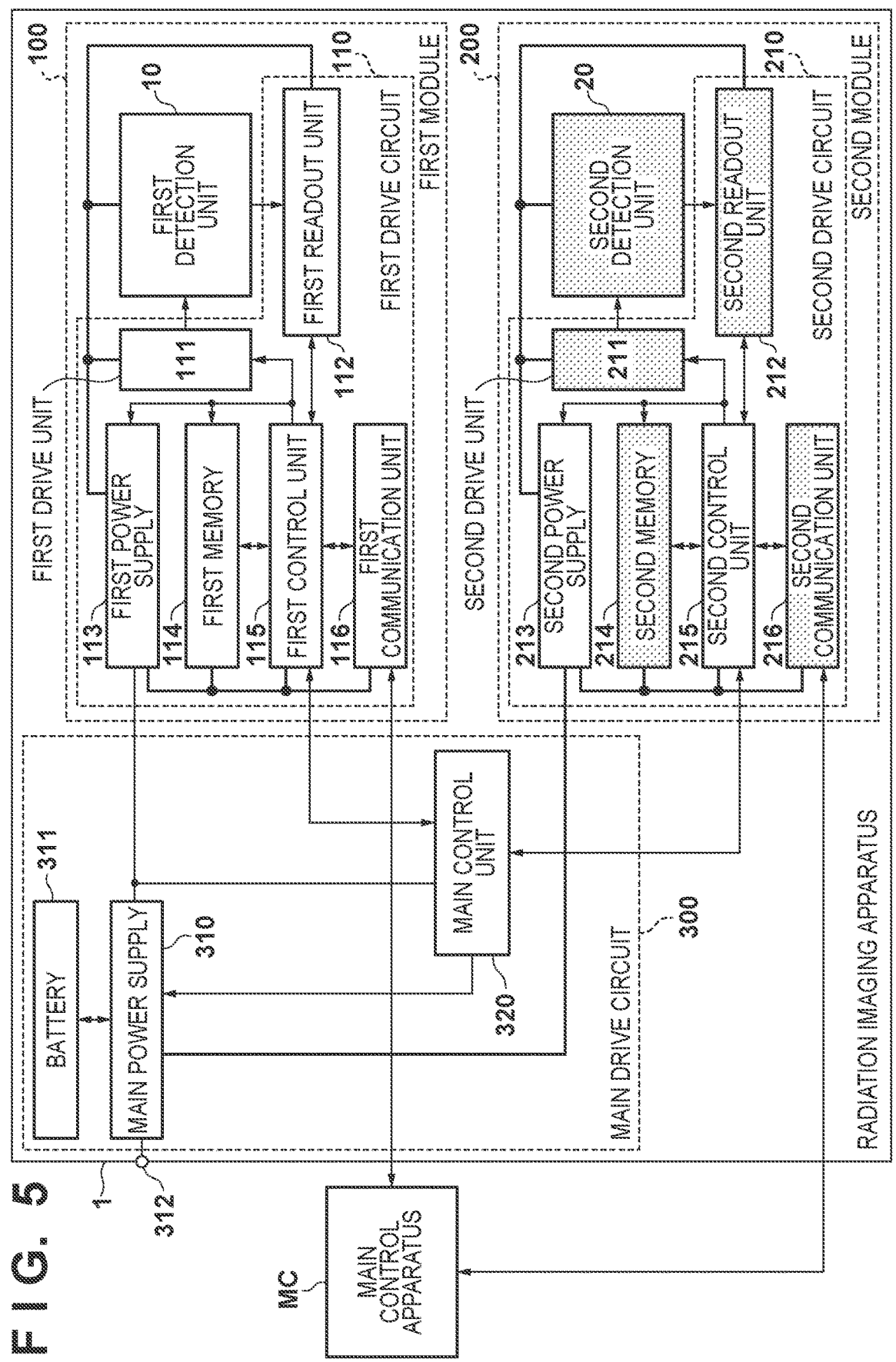
FIG. 5 is a view showing a third example of power supply in the second mode to the second module according to the first embodiment.

FIG. 5 shows a third example of power supply in the second mode to the second module 200 according to the first embodiment. Here, in FIG. 5, power supplied to the constituent elements shown in gray in the second mode is smaller than power supplied to the constituent elements in the first mode, and is, for example, zero. In the third example as well, the main control unit 320 controls the second module 200 such that the power consumption of the second detection unit 20, the second drive unit 211, and the second read unit 212 in the second mode is smaller than the power consumption of the second detection unit 20, the second drive unit 211, and the second read unit 212 in the first mode. This operation can be implemented by the main control unit 320 supplying a control signal to the second power supply 213 and the second power supply 213 operating in accordance with the control signal. Alternatively, this operation can be implemented by the main control unit 320 supplying a control signal to the second control unit 215 and the second control unit 215 controlling the operations of the second memory 214, the second detection unit 20, the second drive unit 211, and the second read unit 212 in accordance with the control signal. In the third example, the second power supply 213 can supply power to the second control unit 215 in the second mode, as in the first mode.

Figure 6:
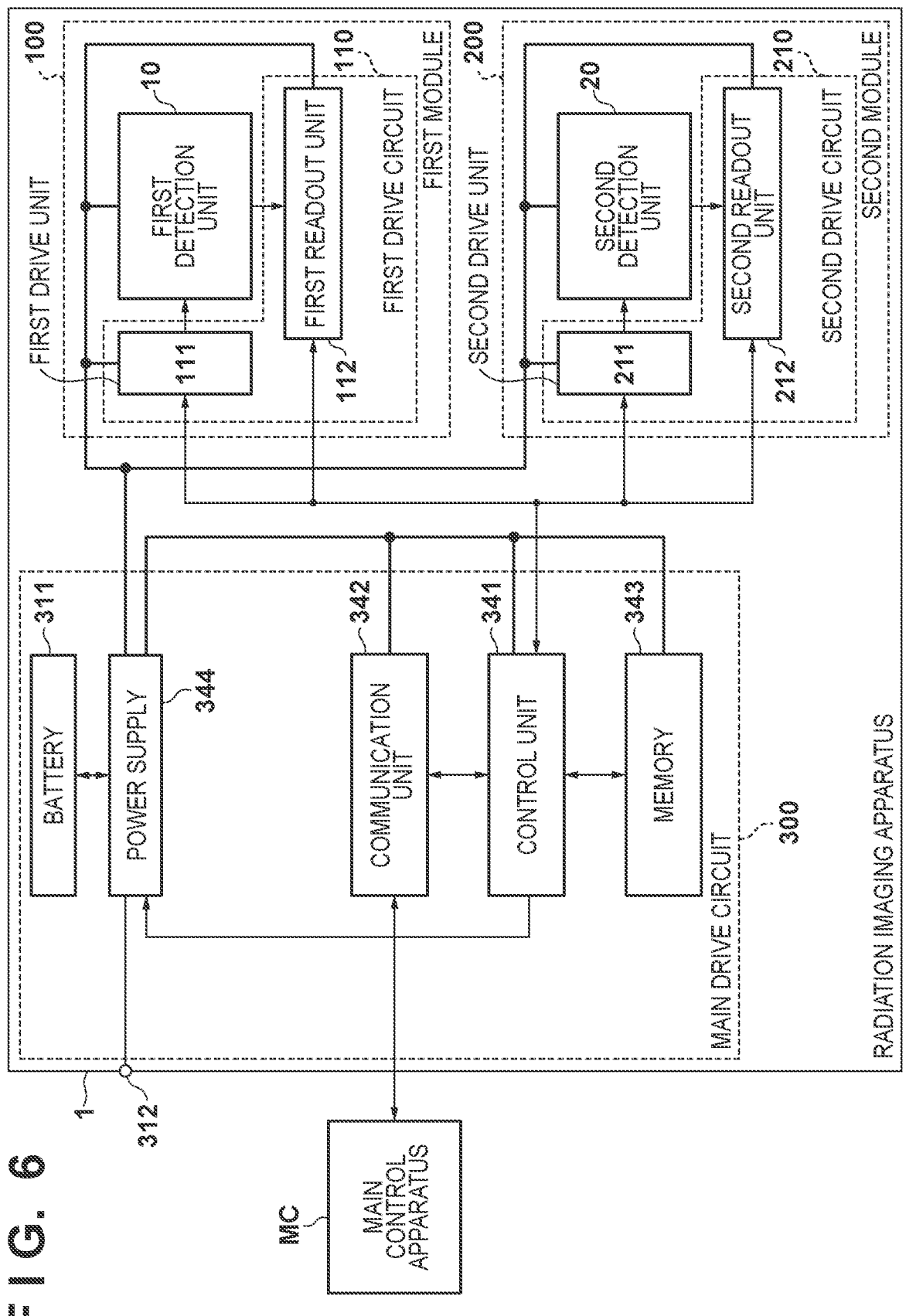
FIG. 6 is a view showing an example of the configuration of a radiation imaging apparatus according to the second embodiment.

FIG. 6 shows an example of the configuration of a radiation imaging apparatus 1 according to the second embodiment. Matters that are not mentioned as the second embodiment can comply with the first embodiment. In the second embodiment, a main drive circuit 300 includes a control unit 341, a communication unit 342, and a memory 343, and the control unit 341, the communication unit 342, and the memory 343 are shared by a first module 100 and a second module 200.

The control unit 341 can operate in accordance with an instruction from a main control apparatus MC. The control unit 341 controls the constituent elements of the main drive circuit 300, and the first module 100 and the second module 200. A signal read out from a first detection unit 10 by a first read unit 112 can be output (transferred) to the main control apparatus MC by the communication unit 342. Similarly, a signal read out from a second detection unit 20 by a second read unit 212 can be output (transferred) to the main control apparatus MC by the communication unit 342. The signal read out from the first detection unit 10 by the first read unit 112 can be stored in the memory 343. Similarly, the signal read out from the second detection unit 20 by the second read unit 212 can be stored in the memory 343.

A power supply 344 can supply power to the constituent elements of the first module 100 and the second module 200 based on power supplied to a connector 312. The power supplied to the connector 312 may be AC power or DC power. The connector 312 and the power supply 344 may be stored in a housing different from that for the remaining portion of the radiation imaging apparatus 1. If the power supplied to the connector 312 is AC power, the power supply 344 can include an AC/DC converter. If the power supplied to the connector 312 is DC power, the power supply 344 can include a DC/DC converter.

A battery 311 may be connected to the power supply 344. If no power is supplied to the connector 312, the power supply 344 can supply power to the first module 100 and the second module 200 based on power output from the battery 311. If power is supplied to the connector 312, and the remaining amount (accumulated power amount) of the battery 311 is less than a predetermined value, the power supply 344 can charge the battery 311 using the power supplied to the connector 312.

Figure 7:
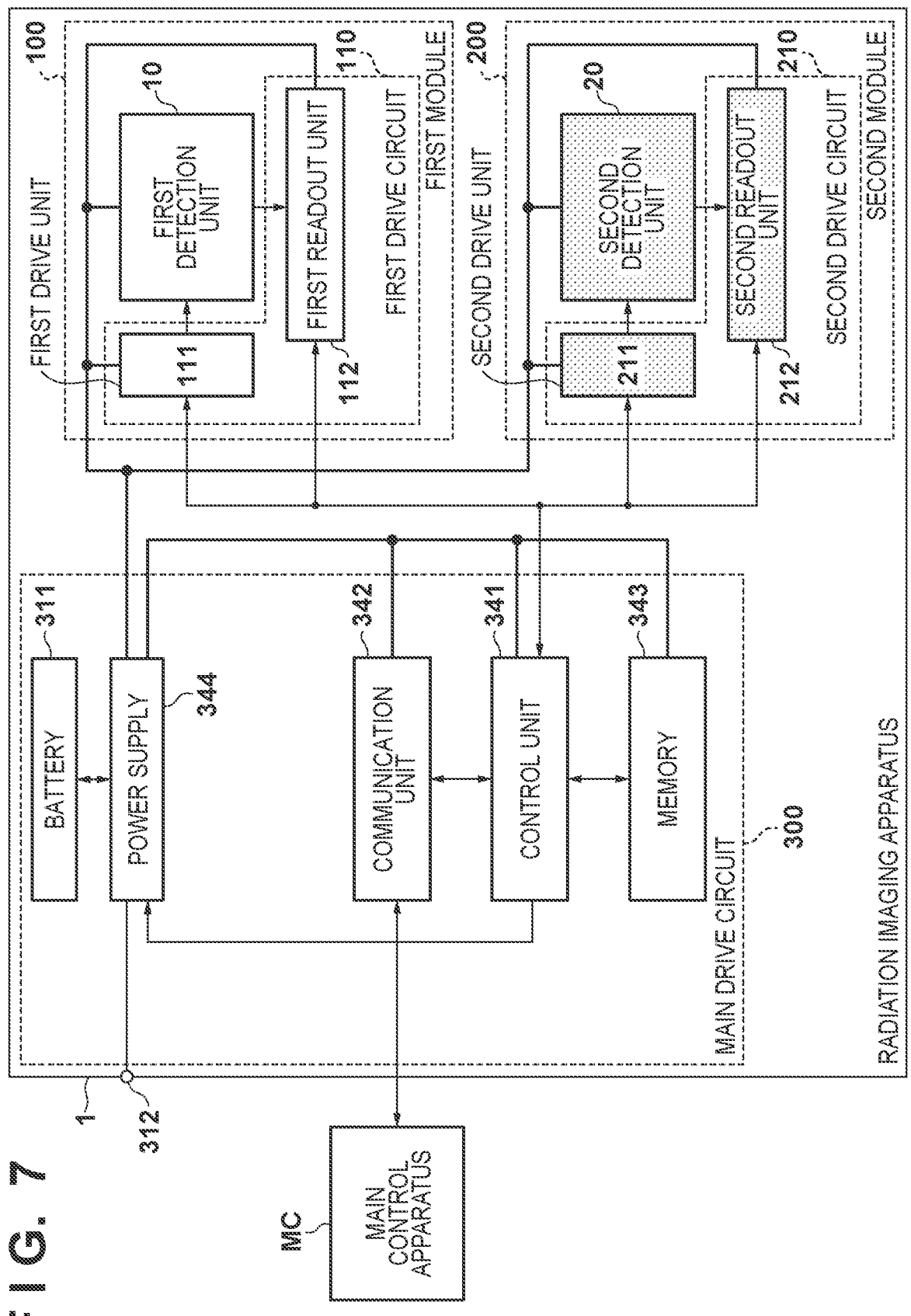
FIG. 7 is a view showing an example of power supply in a second mode to a second module according to the second embodiment.

FIG. 7 shows an example of power supply in the second mode to the second module 200 according to the second embodiment. Here, in FIG. 7, power supplied to the constituent elements shown in gray in the second mode is smaller than power supplied to the constituent elements in the first mode, and is, for example, zero. For example, the power consumption of the second detection unit 20, a second drive unit 211, and the second read unit 212 in the second mode is smaller than the power consumption of the second detection unit 20, the second drive unit 211, and the second read unit 212 in the first mode.

The control unit 341 makes power supplied from the power supply 344 to the second detection unit 20, the second drive unit 211, and the second read unit 212 in the second mode smaller than power supplied from the power supply 344 to the second detection unit 20, the second drive unit 211, and the second read unit 212 in the first mode. This operation can be implemented by, for example, arranging a switch in the power supply path from the power supply 344 to the second module 200 and the control unit 341 controlling the switch.

Figure 8:
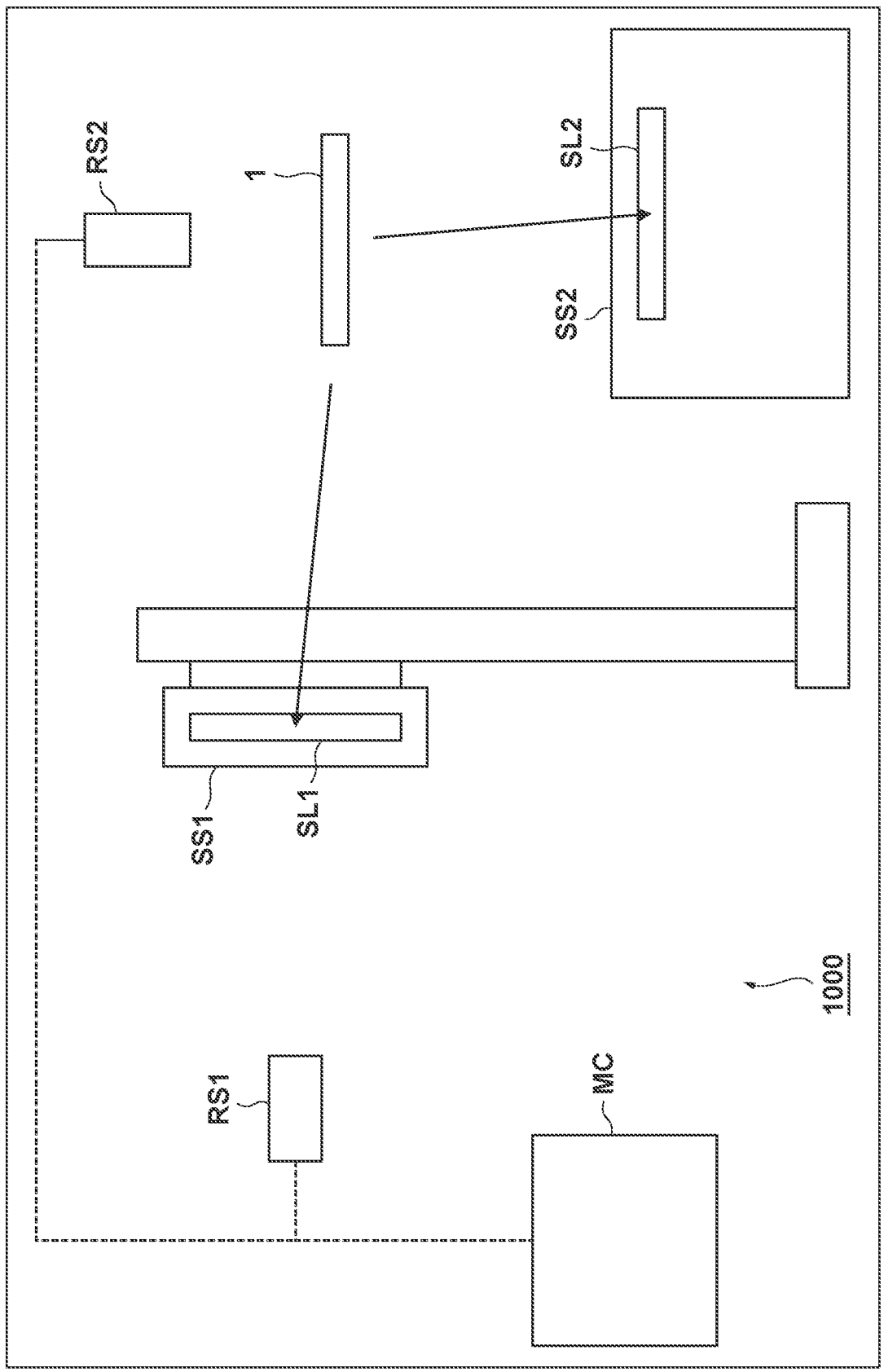
FIG. 8 is a view showing an example of the configuration of a radiation imaging system according to an embodiment.

FIG. 8 shows a radiation imaging system 1000 in which the radiation imaging apparatus 1 according to each of the first and second embodiments can be used. The radiation imaging system 1000 can include one or a plurality of radiation sources RS1 and RS2, the main control apparatus MC, one or a plurality of gantries SS1 and SS2, and the radiation imaging apparatus 1. The gantry SS1 is a gantry used to capture an object in, for example, a standing position, and can include a holding unit SL1 that holds the radiation imaging apparatus 1. The gantry SS2 is a gantry used to capture an object in, for example, a lying position, and can include a holding unit SL2 that holds the radiation imaging apparatus 1. The gantries SS1 and SS2 are examples of gantries used to capture an object in postures different from each other and are also examples of holding the radiation imaging apparatus 1 in postures different from each other.

FIG. 9 is a flowchart showing the operation of the radiation imaging apparatus 1 according to each of the first and second embodiments. The operation shown in this flowchart can be controlled by the main drive circuit 300 (the main control unit 320 or the control unit 341). The main control unit 320 and the control unit 341 can be each controlled by, for example, a PLD (short for Programmable Logic Device) such as an FPGA (short for Field Programmable Gate Array), an ASIC (short for Application Specific Integrated Circuit), or a general-purpose or dedicated computer in which a program is installed, or a combination of some or all of these.

In step S801, the main drive circuit 300 initializes the radiation imaging apparatus 1. In step S802, the main drive circuit 300 determines whether a mode setting instruction is sent from the main control apparatus MC. If a mode setting instruction is sent from the main control apparatus MC, step S803 is executed. Otherwise, step S804 is executed.

In step S803, the main drive circuit 300 selects one mode from a plurality of modes including the first mode and the second mode based on state information, and sets the mode. The state information can be various kinds of information, as will be described below.

As shown in FIG. 1, the radiation imaging apparatus 1 can include a switch 60. The switch 60 can be operated by the user. Information representing the state of the switch 60 is an example of state information. The switch 60 can be, for example, a slide switch, a button switch, or a toggle switch. The switch 60 may be a switch having a first state and a second state. In this case, the first state can designate the first mode, and the second state can designate the second mode. The main drive circuit 300 can set one of the plurality of modes in accordance with the state information representing the state of the switch 60.

As shown in FIG. 8, the radiation imaging apparatus 1 can be arranged on one gantry selected from various kinds of gantries. Each of the gantries SS1 and SS2 can have information for specifying the type of itself. The radiation imaging apparatus 1 can acquire the information representing the type of gantry on which the radiation imaging apparatus 1 is arranged by, for example, communication with the gantry via a communication unit (the first communication unit 116 and the second communication unit 216 in the first embodiment, or the communication unit 342 in the second embodiment). The information representing the type of gantry (for example, a gantry for standing position or a gantry for lying position) is an example of state information.

The main drive circuit 300 can select one mode from the plurality of modes including the first mode and the second mode based on the information representing the type of gantry. Alternatively, the main drive circuit 300 can select one mode from the plurality of modes including the first mode and the second mode based on information representing the posture of the radiation imaging apparatus 1. The posture of the radiation imaging apparatus 1 can be detected by, for example, providing a posture sensor in the radiation imaging apparatus 1 and based on the output of the posture sensor. Alternatively, the posture of the radiation imaging apparatus 1 may be determined based on information provided from the gantry.

The state information may be information representing whether power is supplied to the connector 312. The state information may be information representing the remaining amount of the battery 311, that is, the battery remaining amount. The state information may be information representing the form of communication with the main control apparatus MC that is an external apparatus, for example, wireless communication, wired communication, or the like.

Referring back to FIG. 9, in step S804, the main drive circuit 300 selects one mode from the plurality of modes including the first mode and the second mode based on a mode setting instruction from the main control apparatus MC, and sets the mode. In step S805, the main drive circuit 300 determines whether the first mode is set. If the first mode is set, in step S806, the main drive circuit 300 operates the radiation imaging apparatus 1 in the first mode. On the other hand, if the second mode is set, in step S807, the main drive circuit 300 operates the radiation imaging apparatus 1 in the set mode (for example, the second mode).

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus, comprising:
a first module including a first detection unit configured to detect capture an image formed by radiation that has passed through an object, a first read unit configured to read out signals corresponding to charges accumulated in the first detection unit, and a first memory;
a second module including a second detection unit configured to capture an image formed by radiation that has passed through the object and the first detection unit, a second read unit configured to read out signals corresponding to charges accumulated in the second detection unit, and a second memory; and
a control unit configured to control the first module and the second module in accordance with a mode selected from a plurality of modes including a first mode, wherein
in the first mode the control unit is configured to cause the first and second detection units to respectively capture images, and temporarily store in the first memory signals of the image read out from the first detection unit by the first read unit, while temporarily storing in the second memory signals of the image read out from the second detection unit by the second read unit, and
in the second mode the control unit is configured to cause the first detection unit to capture an image, divides signals of an image read out from the first detection unit by the first read unit into first and second signals, and temporarily store the first signals in the first memory while temporarily storing the second signals in the second memory.

2. The radiation imaging apparatus according to claim 1, wherein power consumption of the second module in the second mode is less than power consumption of the second module in the first mode.

3. The radiation imaging apparatus according to claim 1, wherein the first module includes a first drive unit configured to generate a first drive signal for driving the first detection unit,
the second module includes a second drive unit configured to generate a second drive signal for driving the second detection unit, and
power consumption of the second detection unit, second drive unit, and the second read unit in the second mode is less than power consumption of the second detection unit, second drive unit, and the second read unit in the first mode.

4. The radiation imaging apparatus according to claim 3, wherein the first module further includes a first power supply configured to supply power to the first detection unit, the first drive unit, and the first read unit,
the second module further includes a second power supply configured to supply power to the second detection unit, the second drive unit, and the second read unit, and
the control unit operates the second power supply in the first mode, and does not operate the second power supply in the second mode.

5. The radiation imaging apparatus according to claim 1, wherein a time needed to divide a signal of one image read out from the first detection unit by the first read unit and store the signals in the first memory and the second memory in the second mode is shorter than a time needed to store, in the first memory, the signal of one image read out from the first detection unit by the first read unit in the first mode.

6. The radiation imaging apparatus according to claim 3, wherein the first module further includes a first communication unit configured to transfer the signal read out from the first detection unit by the first read unit,
the second module further includes a second communication unit configured to transfer the signal read out from the second detection unit by the second read unit,
in the first mode the control unit transfers by the first communication unit the signals of the image read out from the first detection unit by the first read unit, and transfers by the second communication unit the signals of the image read out from the second detection unit by the second read unit, and
in the second mode the control unit transfers the first signals by the first communication unit while transferring the second signals by the second communication unit.

7. The radiation imaging apparatus according to claim 6, wherein a time needed to divide the signals of one image read out from the first detection unit by the first read unit and transfer the signals by the first communication unit and the second communication unit in the second mode is shorter than a time needed to transfer the signals of one image read out from the first detection unit by the first read unit by the first communication unit in the first mode.

8. The radiation imaging apparatus according to claim 1, wherein in the first mode the control unit resets the first detection unit and the second detection unit at a first cycle during a period of waiting for radiation irradiation, and in the second mode the control unit resets the second detection unit at a second cycle larger than the first cycle during the period of waiting for radiation irradiation.

9. The radiation imaging apparatus according to claim 8, wherein in the second mode the control unit resets the first detection unit at the first cycle during the period of waiting for radiation irradiation.

10. The radiation imaging apparatus according to claim 1, further comprising a switch, wherein
the control unit is configured to set one of the plurality of modes in accordance with a state of the switch.

11. The radiation imaging apparatus according to claim 1, wherein the control unit is configured to set one of the plurality of modes in accordance with a gantry on which the radiation imaging apparatus is arranged.

12. The radiation imaging apparatus according to claim 1, further comprising a battery and a connector to which power is supplied via a power supply cable, wherein
the control unit is configured to set one of the plurality of modes in accordance with whether the power is supplied to the connector.

13. The radiation imaging apparatus according to claim 1, wherein the control unit is configured to set one of the plurality of modes in accordance with at least one of (a) a battery remaining amount, (b) a form of communication with an external apparatus or (c) a posture of the radiation imaging apparatus.

14. The radiation imaging apparatus according to claim 1, further comprising a display unit, wherein
the control unit is configured to cause the display unit to display the mode selected from the plurality of modes.

15. The radiation imaging apparatus according to claim 1, wherein
the radiation imaging apparatus is configured to be capable of communicating with an information processing apparatus which processes signals output from the radiation imaging apparatus, and the information processing device is configured to generate an image by an energy subtraction method based on the signals read out from the first detection unit and the signals read out from the second detection unit, in a case where the first mode is selected.

16. A control method of a radiation imaging apparatus including a first module having a first detection unit configured to radiation that has passed through an object, a first read unit configured to read out a signal corresponding to charges accumulated in the first detection unit, and a first memory; and a second module having a second detection unit configured to capture the image formed by radiation that has passed through the object and the first detection unit, a second read unit configured to read out a signal corresponding to charges accumulated in the second detection unit, and a second memory, comprising the steps of:

controlling the first module and the second module a first mode such that the first and second detection units are caused to respectively capture images, and signals of the image read out from the first detection unit by the first read unit are temporarily stored in the first memory while signals of the image read out from the second detection unit by the second read unit are temporarily stored in the second memory, and controlling the first module and the second module in a second mode such that the first detection unit caused to capture an image, signals of the image read out from the first detection unit by the first read unit are divided into first and second signals, and the first signal are temporarily stored in the first memory while the second signal are temporarily stored in the second memory.

17. A control apparatus configured to control a first module including a first detection unit configured to capture an image formed by radiation that has passed through an object, a first read unit configured to read out signals corresponding to charges accumulated in the first detection unit, and a first memory; and a second module including a second detection unit configured to capture an image formed by radiation that has passed through the object and the first detection unit, a second read unit configured to read out signals corresponding to charges accumulated in the second detection unit, and a second memory, wherein the apparatus is configured to control the first module and the second module in accordance with a mode selected from a plurality of modes including a first mode and a second mode, in the first mode the apparatus causes the first and second detection units to respectively capture images, and temporarily stores in the first memory signals of the image read out from the first detection unit by the first read unit, while temporarily storing in the second memory signals of the image read out from the second detection unit by the second read unit, and in the second mode the apparatus causes the first detection unit to capture an image, divides signals of an image read out from the first detection unit by the first read unit into first signals and second signals, and temporarily stores the first signals in the first memory while temporarily storing the second signals in the second memory.

18. A control apparatus configured to control a first module including a first detection unit configured to capture an image formed by radiation that has passed through an object, a first read unit configured to read out a signal corresponding to charges accumulated in the first detection unit, and a first communication unit configured to transfer the signals read out from the first detection unit by the first read unit; and a second module including a second detection unit configured to capture an image formed by radiation that has passed through the object and the first detection unit, a second read unit configured to read out signals corresponding to charges accumulated in the second detection unit, and a second communication unit configured to transfer the signal read out from the second detection unit by the second read unit, wherein the apparatus is configured to control the first module and the second module in accordance with a mode selected from a plurality of modes including a first mode and a second mode, in the first mode the apparatus causes the first and second detection units to respectively capture images, and transfers signals of the image read out from the first detection unit by the first read unit while transferring signals of the image read out from the second detection unit by the second read unit, and in the second mode the apparatus causes the first detection unit to capture an image, divides signals of an image read out from the first detection unit by the first read unit into first signals and second signals, and transfers the first signals by the first communication unit while transferring the second signals by the second communication unit.

* * * * *